US012635851B2

(12) United States Patent
Hwang et al.

(10) Patent No.: US 12,635,851 B2
(45) Date of Patent: May 26, 2026

(54) MOBILE AUTOSCOPE SYSTEM

(71) Applicant: Jae Youn Hwang, Daegu (KR)

(72) Inventors: Jae Youn Hwang, Daegu (KR); Thiago Coutinho Cavalcanti, Recife (BR); Hah Min Lew, Seoul (KR)

(73) Assignee: Jae Youn Hwang, Daegu (KR)

( * ) Notice: Subject to any disclaimer, the term of this patent is extended or adjusted under 35 U.S.C. 154(b) by 383 days.

(21) Appl. No.: 18/555,414

(22) PCT Filed: Apr. 15, 2022

(86) PCT No.: PCT/KR2022/005456
§ 371 (c)(1),
(2) Date: Oct. 13, 2023

(87) PCT Pub. No.: WO2022/220639
PCT Pub. Date: Oct. 20, 2022

(65) Prior Publication Data
US 2024/0197152 A1     Jun. 20, 2024

(30) Foreign Application Priority Data

Apr. 16, 2021     (KR) ........................ 10-2021-0049885

(51) Int. Cl.
*A61B 1/00*          (2006.01)
*A61B 1/06*          (2006.01)
(Continued)

(52) U.S. Cl.
CPC ...... *A61B 1/00105* (2013.01); *A61B 1/00016* (2013.01); *A61B 1/0016* (2013.01);
(Continued)

(58) Field of Classification Search
CPC .................................................... A61B 1/227
See application file for complete search history.

(56) References Cited

U.S. PATENT DOCUMENTS 9,445,713  B2     9/2016   Douglas et al.
10,918,272  B2     2/2021   Das et al.
(Continued)

FOREIGN PATENT DOCUMENTS

CN          206178826  U     5/2017
EP            3685729  A1     7/2020
(Continued)

OTHER PUBLICATIONS

Notice of Allowance issued for Korean Patent Application No. 10-2021-0049885 filed on Apr. 16, 2021 on behalf of Daegu Gyeongbuk Institute of Science and Technology. Issuance date: Mar. 7, 2024. 4 pages (Original and English translation).
(Continued)

*Primary Examiner* — Nicholas W Woodall
(74) *Attorney, Agent, or Firm* — Steinfl + Bruno LLP

(57)          ABSTRACT

Disclosed is a mobile autoscope system including: a user terminal device including a camera configured to capture an image of a capture target; and a mobile autoscope detachably mounted on the user terminal device, and configured to emit each of spectral light, ultraviolet (UV) light, or white light to the capture target, wherein the user terminal device is configured to capture the capture target during the emission of spectral light, UV light, or white light to generate a spectral image, a UV excitation fluorescence image, or a three-dimensional (3D) shape image.

9 Claims, 9 Drawing Sheets

(51) Int. Cl.

| | |
|---|---|
| *A61B 1/07* | (2006.01) |
| *A61B 1/227* | (2006.01) |
| *A61B 1/32* | (2006.01) |

(52) U.S. Cl.
CPC .......... *A61B 1/0638* (2013.01); *A61B 1/0646*
(2013.01); *A61B 1/0684* (2013.01); *A61B 1/07*
(2013.01); *A61B 1/227* (2013.01); *A61B 1/32*
(2013.01)

(56)     References Cited

U.S. PATENT DOCUMENTS

| | | | |
|---|---|---|---|
| 11,213,208 B2 | 1/2022 | Hwang et al. | |
| 2009/0131800 A1* | 5/2009 | Liang .................... | A61B 5/0059 600/476 |
| 2016/0255261 A1* | 9/2016 | Govari ................. | A61B 1/0655 348/69 |
| 2017/0071509 A1* | 3/2017 | Pandey ............... | A61B 5/0075 |
| 2019/0090751 A1* | 3/2019 | Hwang ...................... | F21V 5/04 |
| 2019/0167378 A1* | 6/2019 | Wood ..................... | A61B 1/233 |
| 2021/0068645 A1* | 3/2021 | Elson ..................... | A61B 1/227 |
| 2022/0068505 A1* | 3/2022 | Junnarkar ........... | H04M 1/2155 |
| 2023/0172427 A1* | 6/2023 | Clark ..................... | G16H 50/20 600/109 |
| 2023/0301502 A1* | 9/2023 | Rayman ................... | A61B 1/07 |
| 2024/0036297 A1* | 2/2024 | Guo ........................ | G02B 23/08 |
| 2024/0306893 A1* | 9/2024 | Wang ................. | A61B 1/00105 |
| 2025/0025034 A1* | 1/2025 | Arcand ................ | A61B 1/0684 |
| 2025/0261859 A1* | 8/2025 | Guo ........................ | G16H 30/20 |

FOREIGN PATENT DOCUMENTS

| | | | |
|---|---|---|---|
| KR | 101450120 B1 | 10/2014 | |
| KR | 20170030710 A | 3/2017 | |
| KR | 20170057871 A | 5/2017 | |
| KR | 20170104708 A | 9/2017 | |
| KR | 101804094 B1 | 12/2017 | |
| KR | 102036043 B1 | 10/2019 | |
| KR | 102036048 B1 | 10/2019 | |
| KR | 102055185 B1 | 12/2019 | |
| KR | 102113203 B1 | 5/2020 | |
| WO | 2017/189520 A1 | 11/2017 | |
| WO | 2020/148725 A1 | 7/2020 | |

OTHER PUBLICATIONS

Cavalcanti, Thiago C. et al., "Multimode 3D and Spectral Imaging/ Analysis of the tympanic membrane usinga smartphone-based otoscopic system" Daegu Gyeongbuk Institute of Science & Technology. MBIS Lab. Published Date Mar. 8, 2021. 21 pages.

International Search Report and Written Opinion issued for International PCT Application No. PCT/KR2022/005456 filed on Apr. 15, 2022 on behalf of Jae Youn Hwang. Mail Date: Jul. 22, 2022. (English translation and Original), 13 pages.

Office Action issued for KR Application No. 10-2021-0049885 filed on Apr. 16, 2021 on behalf of Daegu Gyeongbuk Institute of Science & Technology. Issuance Date: Mar. 6, 2023. (English translation and Original). 13 pages.

Office Action issued for KR Application No. 10-2021-0049885 filed on Apr. 16, 2021 on behalf of Daegu Gyeongbuk Institute of Science & Technology. Issuance Date: Sep. 7, 2023. (English translation and Original). 12 pages.

* cited by examiner

1000

MOBILE AUTOSCOPE SYSTEM

CROSS REFERENCE TO RELATED APPLICATIONS

The present application is the U.S. national stage of International Application No. PCT/KR2022/005456 filed on Apr. 15, 2022, which, in turn, claims priority to Korean Application No. 10-2021-0049885 filed on Apr. 16, 2021.

TECHNICAL FIELD

Apparatuses and methods consistent with the disclosure relate to a mobile autoscope system, and more particularly, to a mobile autoscope system which may acquire images of various light sources by using a mobile autoscope detachable from a user terminal device.

BACKGROUND ART

An autoscope (or otoscope) refers to an instrument inserted into an external ear canal to inspect or auscultate the ear. In recent years, the autoscope capable of taking a spectral image and a three-dimensional (3D) image has been proposed to help diagnose ear inflammation or hepatitis.

However, a conventional autoscope may be less portable, and have difficulty in observing a chemical state and a 3D structure inside the ear.

DISCLOSURE

Technical Problem

The disclosure provides a mobile autoscope system which may acquire images of various light sources by using a mobile autoscope detachable from a user terminal device.

Technical Solution

According to an embodiment of the disclosure, a mobile autoscope system includes: a user terminal device including a camera configured to capture an image of a capture target; and a mobile autoscope detachably mounted on the user terminal device, and configured to emit each of spectral light, ultraviolet (UV) light, or white light to the capture target, wherein the user terminal device is configured to capture the capture target during the emission of spectral light, UV light, or white light to generate a spectral image, a UV excitation fluorescence image, or a three-dimensional (3D) shape image.

The mobile autoscope may include a probe in contact with the capture target; a plurality of lenses disposed between a tip of the probe and the user terminal device, and configured to concentrate light outside the probe on the camera; a lighting module including a spectral light source, a UV light source, and a white light source; and an optical fiber configured to transmit light emitted from the spectral light source or the UV light source to the tip of the probe.

The UV light source may include a UV light emitting diode (LED) emitting light in a UV band, and the mobile autoscope may further include a first optical filter configured to bandpass filter light emitted from the UV LED, and provide filtered light to the optical fiber, and a second optical filter configured to filter fluorescence light generated by the UV LED and transmit filtered fluorescence light to the camera.

The spectral light source may include a plurality of narrowband LEDs having different center wavelengths.

The white light source may include a plurality of white LEDs disposed at the tip of the probe.

The mobile autoscope may further include a housing having a handle area which is able to be gripped by a user, a gripping member configured to selectively adjusting a distance between a the mobile autoscope and the user terminal device by adjusting a distance between plurality of protruding members, and a motor configured to control the distance between the plurality of protruding members.

The mobile autoscope may further include a button receiving a capture command for a target object; and a communication device configured to transmit the received capture command to the user terminal device.

The mobile autoscope may further include a communication device configured to receive a capture command from the user terminal device, and the mobile autoscope may be configured to control the lighting module to sequentially emit spectral light, UV light, and white light in case that the capture command is received from the user terminal device.

Wherein the user terminal device may be configured to display the plurality of images of different light sources.

The user terminal device may be configured to transmit the generated plurality of images to an external server in case that the plurality of images of different light sources are generated, and display evaluation information in case that the evaluation information on the plurality of images is received from the external server.

Effect of Invention

As set forth above, the mobile autoscope system according to the various embodiments of the disclosure may check the chemical and structural information inside the ear by using a fluorescence image, a spectral image, or a three-dimensional image, thus making the more accurate diagnosis possible. In particular, the mobile autoscope system may be highly portable as the system is operated by being attached to the user terminal device.

BEST MODE

Detailed Description of Exemplary Embodiments

Figure 1:
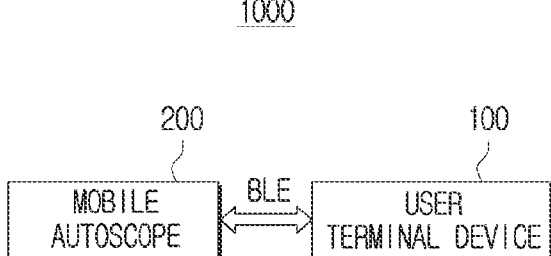
FIG. 1 is a view showing a configuration of a mobile autoscope system according to an embodiment of the disclosure.

Terms used in the specification are briefly described, and the disclosure is then described in detail.

General terms that are currently widely used are selected as terms used in embodiments of the disclosure in consideration of their functions in the disclosure, and may be changed based on the intention of those skilled in the art or a judicial precedent, the emergence of a new technique, or the like. In addition, in a specific case, terms arbitrarily chosen by an applicant may exist. In this case, the meanings of such terms are mentioned in detail in corresponding descriptions of the disclosure. Therefore, the terms used in the disclosure need to be defined on the basis of the meanings of the terms and the contents throughout the disclosure rather than simple names of the terms.

The disclosure may be variously modified and have various embodiments, and specific embodiments of the disclosure will be shown in the drawings and described in detail in the detailed description. However, it is to be understood that the disclosure is not limited to the specific embodiments, and includes all modifications, equivalents, and substitutions without departing from the scope and spirit of the disclosure. In case that it is decided that a detailed description for the known art related to the disclosure may obscure the gist of the disclosure, the detailed description will be omitted.

Terms "first," "second," and the like, may be used to describe various components. However, the components are not to be construed as being limited by these terms. The terms are used only to distinguish one component from another component.

A term of a singular number may include its plural number unless explicitly indicated otherwise in the context. It is to be understood that a term "include" or "formed of" used in the specification specifies the presence of features, numerals, steps, operations, components, parts, or combinations thereof, which is mentioned in the specification, and does not preclude the presence or addition of one or more other features, numerals, steps, operations, components, parts, or combinations thereof.

In the embodiments of the disclosure, a "module" or a "~er/or" may perform at least one function or operation, and be implemented by hardware or software, or be implemented by a combination of hardware and software. In addition, a plurality of "modules" or a plurality of "~ers/ors" may be integrated in at least one module and implemented by at least one processor except for a "module" or an "~er/or" that needs to be implemented by specific hardware.

Hereinafter, the embodiments of the disclosure are described in detail with reference to the accompanying drawings for those skilled in the art to which the disclosure pertains to easily practice the disclosure. However, the disclosure may be modified in various different forms, and is not limited to the embodiments provided in the specification. In addition, in the drawings, portions unrelated to the description are omitted to clearly describe the disclosure, and similar portions are denoted by similar reference numerals throughout the specification.

Hereinafter, the embodiments of the disclosure are described in detail with reference to the accompanying drawings.

FIG. 1 is a view showing a configuration of a mobile autoscope system according to an embodiment of the disclosure.

Referring to FIG. 1, a mobile autoscope system 1000 may include a user terminal device 100 and a mobile autoscope 200.

The user terminal device 100 may include a camera, and may capture an image by using the camera. The user terminal device may be any of various electronic devices carried by a user, such as a smartphone, a laptop personal computer, and the camera.

In addition, the user terminal device 100 may display a captured image, and determine a state of a target object by performing analysis on the captured image.

Such determination may be performed by the user terminal device 100 on its own or with the help of an external device. For example, in case of performing the determination on its own, the user terminal device 100 may perform the analysis by inputting generated image data into a learning model and display an analysis result.

In case of performing the determination by using the external device, the user terminal device 100 may provide the generated image data to the external device, and receive and display the analysis result from the external device.

Meanwhile, the user terminal device 100 may perform image processing on generated image before the image analysis. For example, the user terminal device 100 may perform a three-dimensional (3D) shape reconstruction operation of an image captured through a white light source by using a photometric algorithm, and also perform the image processing such as achromatic conversion, shading, or the like on an image captured through a spectral light source.

The description describes the specific configuration and operation of the user terminal device 100 below with reference to FIG. 2.

The mobile autoscope 200 may be detachably mounted on the user terminal device 100. In addition, in case of receiving a capture command (or a light emission command), the mobile autoscope 200 may emit spectral light, ultraviolet (UV) light, or white light to a capture target.

Here, the capture command may be input through a button positioned on the mobile autoscope 200, or may be input through a button mounted on the user terminal device 100 or by selection of a user interface (UI) icon. In detail, in case of receiving the capture command through the button positioned on the mobile autoscope 200, the mobile autoscope 200 may notify information in which the capture command is input to the user terminal device 100. On the other hand, in case that the capture command is input to the user terminal device 100, the user terminal device 100 may transmit the light emission command to sequentially emit light to the mobile autoscope 200.

Here, the spectral light may emit light of different wavelengths. For ease of explanation, the description describes that the spectral light is emitted using one light source. However, a spectral image may be generated in case that the plurality of images are generated by using light of different bands, and actually generated in a process in which different bands emit light multiple times.

In addition, light may be implemented to be emitted in a different order from the above-mentioned order, and spectral light may emit light of different bands. Therefore, emission using UV light or emission using the white light source may be performed in a process in therebetween.

The description describes specific configuration and operation of the mobile autoscope 200 below with reference to FIGS. 3 to 7.

The mobile autoscope system according to an embodiment of the disclosure as described above may generate the image of the capture target by using not only the white light source but also UV light or spectral light, thus acquiring not only morphological information of a tissue in an ear, but also quantitative information on a biological/physiological state of the ear. In addition, the mobile autoscope system may be highly portable and easily available in an area where there is a shortage of professional medical personnel, in that this system is operated by being attached to the user terminal device carried by the user.

Figure 2:
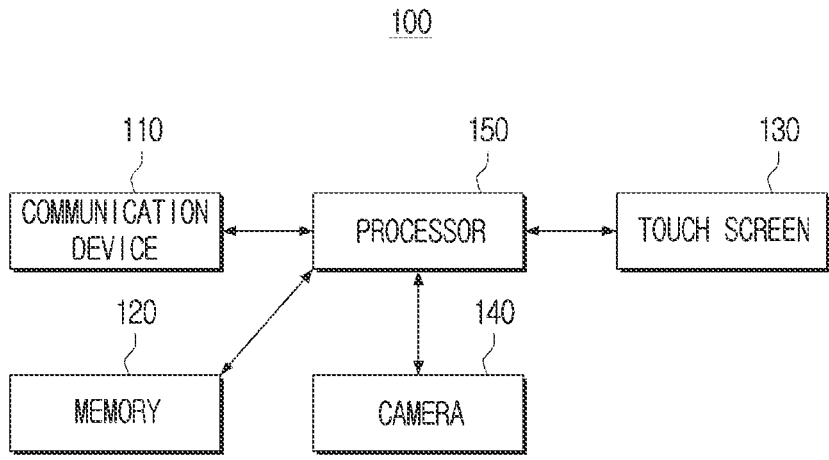
FIG. 2 is a view showing a configuration of a user terminal device of FIG. 1.

FIG. 2 is a view showing a configuration of the user terminal device of FIG. 1.

Referring to FIG. 2, the user terminal device 100 may include a communication device 110, a memory 120, a touch screen 130, a camera 140, and a processor 150. Here, the user terminal device is an electronic device carried by the user, and including the camera, and may be the smartphone, the laptop PC, a tablet PC, a digital camera, or the like.

The communication device 110 may be connected to the mobile autoscope 200, and may transmit and receive a necessary control command during capturing the image. In detail, the communication device 110 may connect the user terminal device 100 with the external device, and may be connected to another electronic device through a local area network (LAN), an internet network, a Bluetooth, or the like as well as through a universal serial bus (USB) port. Meanwhile, the communication device 110 may be implemented to communicate with the mobile autoscope 200 by using another P2P communication method such as wireless fidelity (WiFi) direct in addition to the Bluetooth.

In addition, the communication device 110 may transmit various images generated in a process described below to the external device and receive the analysis result for the image from the external device.

The memory 120 is a component storing an operating system (O/S) for driving the user terminal device 100, software for performing voice recognition/subtitle synchronization, data, or the like. The memory 120 may be implemented in various forms such as a random access memory (RAM), read-only memory (ROM), a flash memory, a hard disk drive (HDD), an external memory, or a memory card, and is not limited to any one of them.

In addition, the memory 120 may store applications for performing various functions, and one of these applications may be an inspection application for capturing the image and performing the analysis thereon by using the mobile autoscope 200 as described above.

The memory 120 may store the captured image. Here, the image may include a shape image such as the spectral image captured with light of different bands, a UV excitation fluorescence image captured during a process of emitting UV light, or a shape image including a 3D image captured with light from the white light source. Here, the UV excitation fluorescence image may be a fluorescence image excited at the capture target (in detail, an eardrum) by emission of a UV light source.

The memory 120 may store the learning model for analyzing the generated image. Here, the learning model may detect a specific disease by using the UV excitation fluorescence image, the spectral image, or the 3D shape image. In case that one learning model may detect only one disease, the memory 120 may include the plurality of learning models. Such a learning model may be received from an external server and stored in the memory 120.

The touch screen 130 may display a user interface window for selecting a function supported by the user terminal device 100. In detail, the touch screen 130 may display the user interface window for selecting various functions provided by the user terminal device 100, and may display the captured image and/or the analysis result of the image.

The camera 140 may generate the image by capturing the captured image. In detail, the camera 140 may include an image sensor and a plurality of lenses forming an image of light on the image sensor. If the plurality of cameras are positioned on the user terminal device, the capturing may be performed by selecting the camera that is advantageous for close-up capturing or has the highest resolution.

The processor 150 may control each component in the user terminal device 100. In detail, processor 150 may perform booting by using the operating system stored in the memory 120 in case of receiving a boot command from the user.

In case that the inspection application is executed, the processor 150 may perform various operations based on the operation of the inspection application. The above-mentioned inspection application may perform a pairing operation for connection of the user terminal device 100 with the mobile autoscope 200, a mounting operation for accurate mounting of the user terminal device 100 with the mobile autoscope 200, a light source module control operation and a camera control operation, based on the user's capture command after the mounting, an image processing operation and an analysis operation for the generated image, or the like. Hereinafter, the description describes each operation in detail.

In case that there is no communication connection with the mobile autoscope 200 or a Bluetooth communication function is turned off, the processor 150 may request communication connection from the user. In addition, in case that there is a wireless connection history between the mobile autoscope 200 and the user terminal device 100, the processor 150 may perform automatic connection with the mobile autoscope 200 in response to the execution of the above-described inspection application.

In case that the user terminal device 100 is mounted on the mobile autoscope 200, the processor 150 may determine whether the lens of the camera 140 and a probe of the mobile autoscope 200 are aligned with each other. In detail, the processor 150 may analyze the captured image to determine whether the probe and the camera are aligned with each other.

In case of determining that the probe and the camera are not aligned with each other as a determination result, the processor 150 may request the alignment of the mobile autoscope 200 and the user terminal device 100 from the user, or automatically align the mobile autoscope 200 and the user terminal device 100 with each other.

Meanwhile, a gripping member of the mobile autoscope 200 may be moved in x and y axes, thus adjusting dispositions of the mobile autoscope 200 and the user terminal device 100. In this case, the processor 150 may control the communication device 110 to transmit a movement command for aligning the mobile autoscope 200 and the user terminal device 100 to the mobile autoscope 200. For example, in case of confirming a bias of about 5 mm to the left or right between the probe of the mobile autoscope 200 and the camera, the processor 150 may transmit the movement command to the mobile autoscope 200 to compensate for the above-described bias. Meanwhile, the processor 150 may be implemented to adjust a position of the probe on a housing of the autoscope 200, rather than positions of the mobile autoscope 200 and the user terminal device 100. In detail, the position of the probe on the housing may be implemented to be adjustable, or a probe housing (or a probe module) including the probe may be implemented to be replaceable.

In case of receiving the capture command from the user, the processor 150 may transmit, to the mobile autoscope 200, a command to emit light in a predefined order. For example, the processor 150 may transmit, to the mobile autoscope 200, a command to emit light in an order of spectral light in a first band, spectral light in a second band, spectral light in a third band, spectral light in a fourth band, UV light, and white light in a predetermined time unit after the command.

Meanwhile, the processor 150 may be implemented to transmit the command step by step. For example, the processor 150 may transmit the command to emit spectral light in the first band to the mobile autoscope 200 and receive a response from the mobile autoscope 200 that spectral light in the first band is emitted. In this case, the processor 150 may control the camera 140 to generate an image of spectral light in the first band, and repeatedly transmit the command to emit spectral light in the second band to the mobile autoscope 200 in case of completing a capturing operation. A specific operation is described below with reference to FIG. 9.

In case of completing the capturing operation, the processor 150 may selectively perform the analysis on the image on its own, or transmit the generated image to the external server to perform the analysis.

In addition, before the above-described analysis process, the processor 150 may perform the image processing or the like on the image. For example, the processor 150 may perform the image processing such as the achromatic conversion, the shading, and correction on the spectral image, and perform the 3D shape reconstruction operation by using a 3D restoration algorithm on the 3D shape image (or the image using the white light source).

In addition, the processor 150 may control the touch screen 130 to display the analysis result.

The user terminal device 100 according to this embodiment as described above may generate the image by using not only the white light source but also UV light or spectral light, thus acquiring not only the morphological information of the tissue in the ear, but also the quantitative information on the biological/physiological state of the ear.

Meanwhile, the description describes that the user terminal device 100 includes only the touch screen with reference to FIG. 2. However, the touch screen may be implemented as a display and a manipulation device (e.g., keyboard, mouse, or plurality of buttons). In addition, the user terminal device 100 may further include another component, such as a power button, a volume control button, or the like, in addition to the components described above, and the above-described power button or volume control button may be used as a button to receive the capture command in case that the above-described inspection application is operated.

Figure 3:
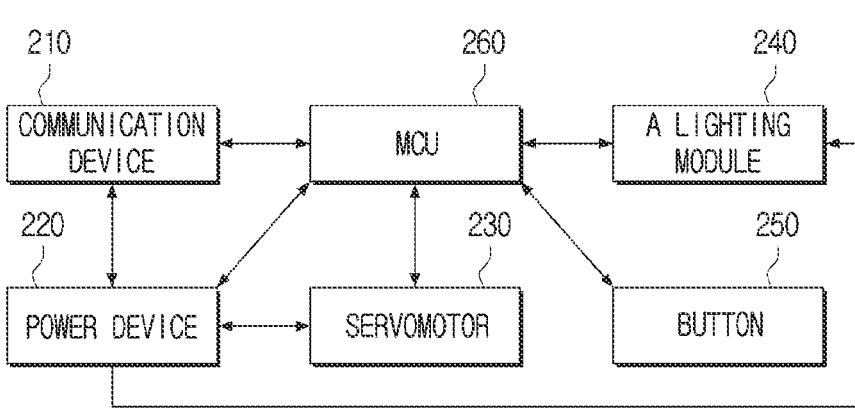
FIG. 3 is a view showing a specific configuration of a mobile autoscope of FIG. 1.

FIG. 3 is a view showing a specific configuration of the mobile autoscope of FIG. 1.

Referring to FIG. 3, the mobile autoscope 200 may include a communication device 210, a power device 220, a servomotor 230, a lighting module 240, a button 250, and a motor controller unit (MCU) 260.

The communication device 210 may be connected to the user terminal device 100, and may transmit or receive various control commands required during capturing the image. In detail, the communication device 210 may include a Bluetooth module, and may be connected to the user terminal device 100 through the Bluetooth. The communication device 210 may not only be implemented to use a P2P communication method such as the WiFi Direct in addition to the Bluetooth module, but also be implemented to be connected by a wired method (for example, a universal serial bus (USB) communication).

The power device 220 may supply power to various electronic components in the mobile autoscope 200. For example, the mobile autoscope 200 may be connected to the user terminal device 100 through a wired cable. In this case, the mobile autoscope 200 may receive power from the user terminal device 100 through the wired cable, and may convert received power to have a voltage level suitable for each internal component and provide converted power to each component.

Alternatively, the power device 220 may include a battery, convert battery power to have a voltage level suitable for each component, and provide converted battery power to each component.

The servomotor 230 may adjust a distance between a plurality of protruding members in the gripping member. For example, the servomotor 230 may only adjust the distance between the protruding members in case that the distance between the plurality of protruding members is adjustable, and may provide a driving force for adjusting a position of each of the plurality of protruding members in case that the position of each of the plurality of protruding members is adjustable. For example, in case that x and y coordinates of the plurality of protruding members are adjustable, the servomotor 230 may perform positional alignments of the camera of the user terminal device 100 and the probe. Meanwhile, the description hereinabove describes that the distance is adjusted using the servomotor 230. However, the server motor shown in FIG. 3 may be implemented to use various other motors such as a direct current (DC) motor or a step motor in addition to the servomotor, and may also be referred to as a motor.

Here, the protruding member may be a component fixing the user terminal device 100, and may selectively fix or separate the user terminal device 100 by adjusting the distance between the two protruding members. The protruding members may be used to align the camera and the probe as described above if the position of each of the two protruding members may be adjusted individually rather than only the distance between the protruding members.

The lighting module 240 may be a component emitting light to the capture target by using the plurality of light sources, and may include the spectral light source, the UV light source, and the white light source.

The spectral light source may include a plurality of narrowband light emitting diodes (LEDs) having different center wavelengths. Here, each narrowband LED may include a first LED having a central wavelength of 440 nm, a second LED having a central wavelength of 460 nm, a third LED having a central wavelength of 480 nm, a fourth LED having a central wavelength of 515 nm, a fifth LED having a central wavelength of 550 nm, a sixth LED having a central wavelength of 585 nm, a seventh LED having a central wavelength of 620 nm, an eighth LED having a central wavelength of 655 nm, and a ninth LED having a central wavelength of 690 nm. Here, each narrowband LED may have a bandwidth of 9 to 19 nm. Meanwhile, the number of center bands and narrow band LEDs described above is an example, and the lighting module 240 may be implemented to use a band different from the center band described above, and also use the different number. The lighting module 240 may acquire nine spectral images in case that the spectral light source includes nine narrow band LEDs as described above.

Meanwhile, the description hereinabove describes that the spectral light source is implemented using the plurality of narrowband LEDs. However, the spectral light source may also be implemented to use one single light source and a plurality of optical filters.

The UV light source may include a UV LED emitting light in a UV band. Here, the UV LED may be a light source which may emit light in the ultraviolet band having a wavelength shorter than that of visible light, and may acquire an ultraviolet ray and the fluorescence image by using the UV light source. An ultraviolet image may be useful for diagnosing a skin disease which is not visible to a naked eye, and thus may be useful for examining the skin disease in the ear. In addition, the fluorescence image generated by excitation in the ear tissue by the UV light source may be useful in diagnosing an ear disease. The lighting module 240 may be implemented to filter UV light among light flowing into the camera to acquire the fluorescence image by using the UV light source, and a fluorescence filter transmitting only fluorescence light longer than UV light is disposed between the probe and the camera.

The white light source may include a plurality of white LEDs. Here, the white LEDs may include a plurality of LEDs having the same wavelength, or include combination of LEDs outputting light in different wavelengths. The white light source may be disposed at a tip of the probe. The description describes this disposition structure below with reference to FIG. 6.

The button 250 may receive the user's manipulation command, and this button may be disposed to be easily manipulated if the user grips the mobile autoscope 200 in case that the button is connected to the MCU 260 described below.

The MCU 260 may control each component in the mobile autoscope 200. In detail, in case that the user command is input through the button 250, the MCU 260 may control the communication device 210 to transmit the input command to the user terminal device 100.

In addition, the MCU 260 may control the lighting module 240 to emit light from the light source in the predetermined order or light from the light source corresponding to the command in case that an operation command for a light source is input through the communication device 210.

In addition, the MCU 260 may control the servomotor 230 to move the protruding member based on the command in case of receiving a grip command or a position adjustment command through the communication device 210.

The mobile autoscope 200 according to this embodiment as described above may emit not only the white light source but also UV light or spectral light, thus generating a UV image or the spectral image for easy analysis of the morphological information of the tissues inside the ear, but also the quantitative information on the biological/physiological state of the ear.

Meanwhile, the description describes that the probe of the mobile autoscope and the camera of the user terminal device are aligned by adjusting the mounting positions of the user terminal device and the mobile autoscope with reference to FIGS. 1 to 3. However, the user terminal device and the mobile autoscope may be implemented to have fixed mounting positions while adjusting the position of the probe. In this case, the above-described servomotor may adjust x and y positions of the probe.

Figure 4:
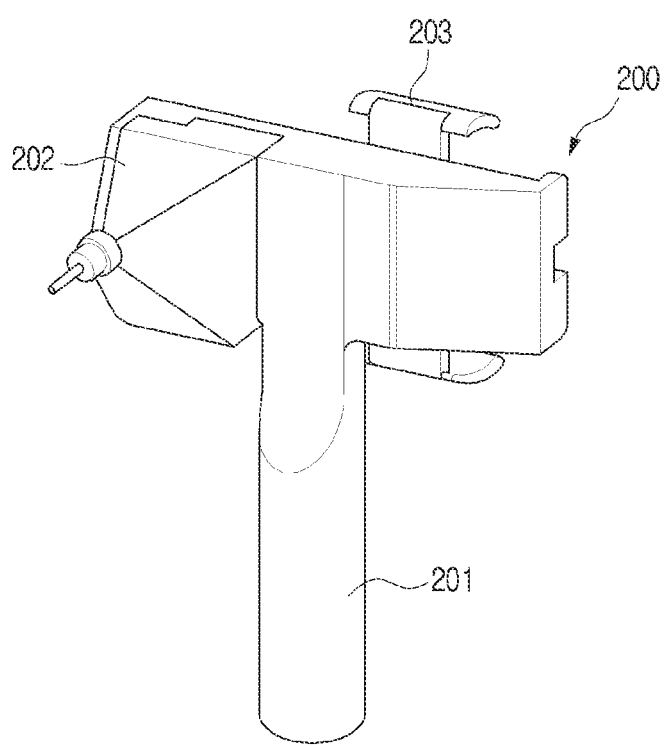
FIG. 4 is a view showing a shape of the mobile autoscope of FIG. 1.

FIG. 4 is a view showing a shape of the mobile autoscope of FIG. 1.

Referring to FIG. 4, the mobile autoscope 200 may have a housing 201 including a handle area which may be gripped by the user.

The battery may be disposed in the handle area in this housing, a probe 202 may be positioned on a front side of the mobile autoscope 200, and a gripping member 203 for the coupling of the mobile autoscope 200 with the user terminal device 100 may be disposed on the opposite side.

For aligning the probe 202 and the camera of the user terminal device 100, the alignment may be performed by moving a position of the protruding member of the gripping member 203, or by adjusting a position of the probe 202.

The mobile autoscope 200 according to the disclosure as described above may be highly portable by having a shape in which the mobile autoscope 200 may be easily gripped by the user.

Figure 5:
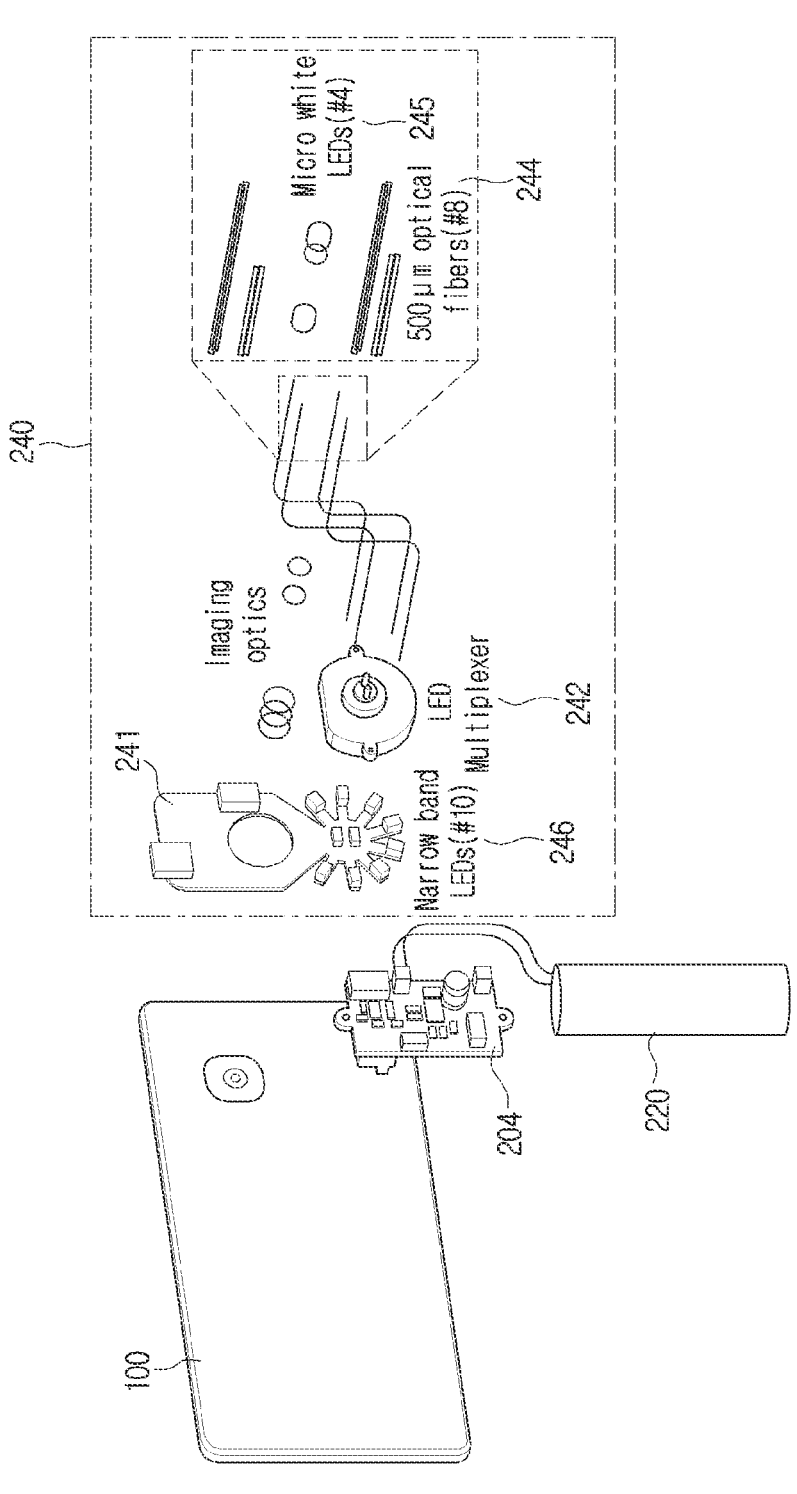
FIG. 5 is a view showing an arrangement form between the mobile autoscope and the user terminal device and a specific optical configuration of the mobile autoscope according to an embodiment of the disclosure.

FIG. 5 is a view showing an arrangement form between the mobile autoscope and the user terminal device and a specific optical configuration of the mobile autoscope according to an embodiment of the disclosure.

Referring to FIG. 5, the mobile autoscope 200 may include the power device 220, a first substrate 204, the lighting module 240, the plurality of lenses, and an optical filter.

In case that the first substrate 204 receives power from the power device 220, the MCU 260 and the communication device 210 described with reference to FIG. 3 may be disposed.

The plurality of lenses and the optical filter may form the image of light from outside the probe on the camera of the user terminal device 100. Here, one of the optical filters may be a second optical filter (that is, the fluorescence filter). In detail, the fluorescence filter may be an optical filter removing UV light from light incident through the probe, and transmitting only fluorescence light with a longer wavelength than UV light. In detail, a position of the second optical filter may be adjusted by a movement member in case that the fluorescence filter not only removes UV light but also filters light in a visible light band. For example, the optical filter may be disposed outside a position between the camera and the probe during the generation of the spectral image or the 3D shape image by the emission of spectral light or emission of white light, and the optical filter may be disposed between the camera and the probe during a process of generating the UV excitation fluorescence image by using UV light. The disposition of the optical filter may be moved by a driving member such as the motor.

The lighting module 240 may include a second substrate 241, a plurality of light sources 245 and 246, an LED multiplexer 242, and a plurality of optical fibers 244.

The second substrate 241 may include a hole in the center, and the plurality of light sources may be disposed to be spaced apart from the hole. Here, the plurality of light sources may include the plurality of narrow band LEDs and UV LEDs for spectral light.

The LED multiplexer 242 may be a structure allowing prism-shaped light to be totally reflected into the inside, have one side connected to the optical fiber 244, have an upper part inclined to direct light to the corresponding optical fiber, and have the inside coated with a reflective coating material.

The plurality of optical fibers 244 may transmit light from the light source disposed on the second substrate 241 to a tip of the probe 202.

The description describes a shape of the tip of probe 202 below with reference to FIG. 6.

Figure 6:
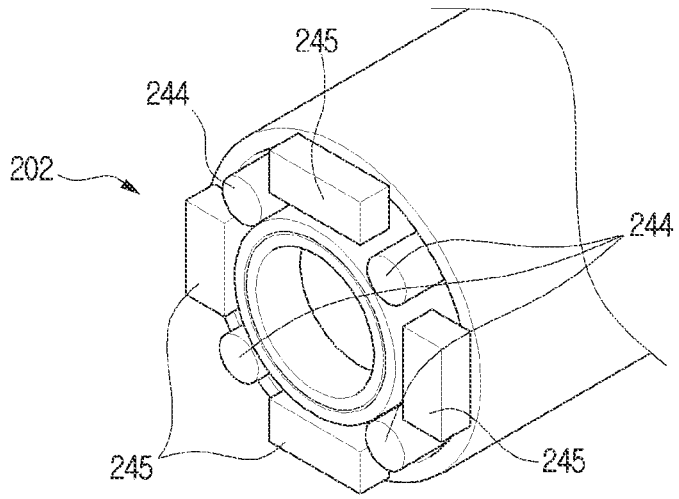
FIG. 6 is a view showing a shape of a tip of a probe according to an embodiment of the disclosure.

FIG. 6 is a view showing the shape of the tip of the probe according to an embodiment of the disclosure.

Referring to FIG. 6, the tip of the probe 202 may have a double cylindrical shape. Here, an inner cylinder may be a passage through which light from outside the probe is moved toward the lens, and a space between the two cylinders may be an area where light from the light source is emitted outside the probe. In detail, a tip of the optical fiber 244 that transmits light of the LED disposed in the mobile autoscope may be disposed in a corresponding area, and the white light source 245 may also be disposed in a corresponding area.

In this way, the white light source 245 may include four LEDs or may also be include five or more LEDs to minimize a sound range. Meanwhile, the white LED may be implemented to be also disposed on the second substrate rather than the tip of the probe, and light may be emitted to the outside through the optical fiber.

Figure 7:
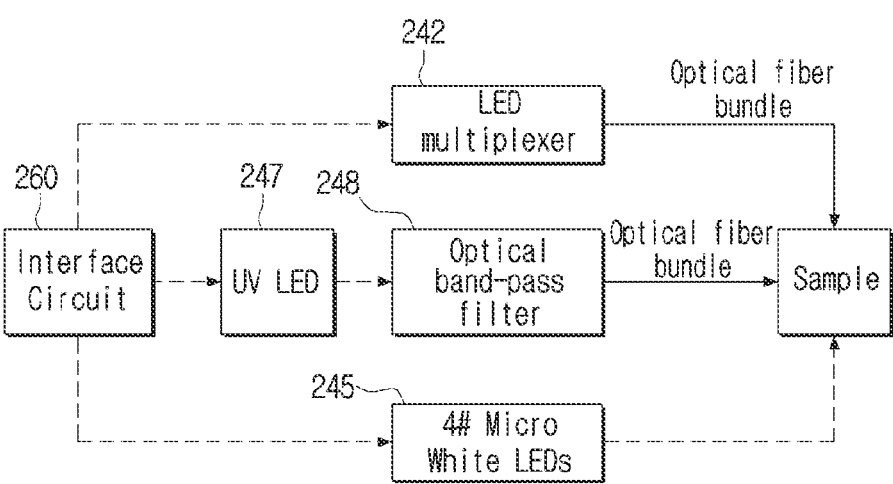
FIG. 7 is a view for explaining an operation of the mobile autoscope of FIG. 1.

FIG. 7 is a view for explaining the operation of the mobile autoscope of FIG. 1.

Referring to FIG. 7, the communication device 210 and the MCU 260 may be disposed at an interface circuit 260. The interface circuit receive a light source emission command from the user terminal device 100. In case of receiving the light source emission command, the interface circuit may control the LED multiplexer to emit spectral light, then control the UV LED to emit UV light, and control the plurality of white LEDs to emit the white light source. Light may be implemented to be emitted in the above-mentioned order, that is, spectral light, UV light, and white light may be sequentially emitted. Alternatively, light may be emitted in an order different from the above-mentioned order, that is, UV light, white light, spectral light, or UV light, spectral light, and white light may be sequentially emitted. In addition, the light emission may proceed by adding another light source in addition to the light sources described above.

The UV light source may filter light emitted from the UV LED through a first optical filter (in detail, optical band pass filter) 248 and emit the same to the outside. Although not shown in FIG. 7, which is a view related to the light source emission of the lighting module, fluorescence light excited in a sample by UV light emitted from the UV light source may remove UV light therefrom by the second optical filter (i.e., fluorescence filter) disposed between the camera and the probe, and only fluorescence light having a longer wavelength than UV light may thus be transmitted to the camera.

Figure 8:
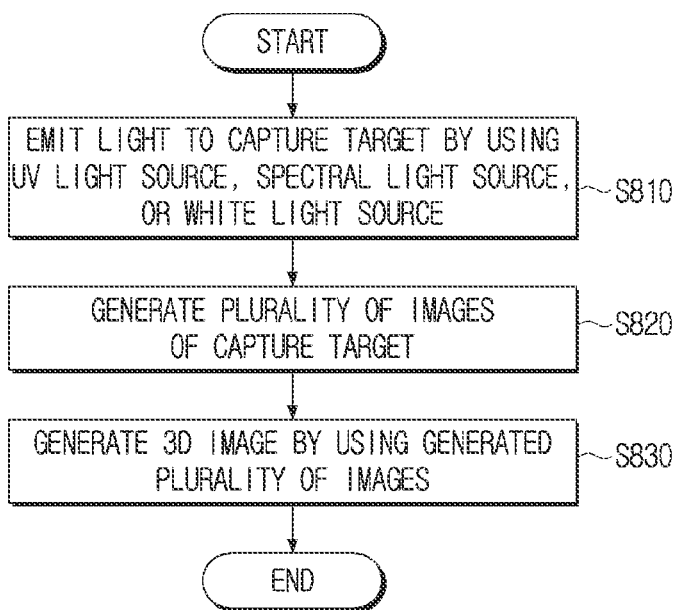
FIG. 8 is a view for explaining a method of generating an image according to an embodiment of the disclosure; and, FIG. 9 is a sequence diagram for explaining an operation performed between the user terminal device and the mobile autoscope according to an embodiment of the disclosure.

FIG. 8 is a view for explaining a method of generating the image according to an embodiment of the disclosure.

Referring to FIG. 8, light may be first emitted to the capture target by using the UV light source, the spectral light source, or the white light source (S810). In detail, UV light may be emitted using the UV light source, spectral light of different bands may then be emitted, and UV light may then be emitted. Light may be implemented to be emitted in an order different from the above-described emission order, and the emission of the UV light source and the emission of the white light source may be performed between the nine spectral light emissions. Meanwhile, the optical filter (in detail, fluorescence filter) for acquiring the fluorescence image may be implemented to be disposed on a front part of the lens in case of the emission of the UV light source. The optical filter may filter fluorescence light generated from the UV LED and transmit the same to the camera.

The plurality of images may be generated by capturing the capture target in response to the emission of light described above (S820). For example, a total of eleven images may be generated in case that spectral light is emitted in nine different bands.

The image processing on the image, such as the 3D reconstruction operation using the 3D restoration algorithm may then be performed on the 3D shape image generated using the white light source among the generated plurality of images (S830).

The analysis of the target object may then be performed through the analysis of the image-processed image. The analysis may be performed by the user terminal device 100 on its own, and may also be performed by the external device by transmitting the image to the external device.

In addition, in case that the analysis is completed, the analysis result may be displayed to the user.

Figure 9:
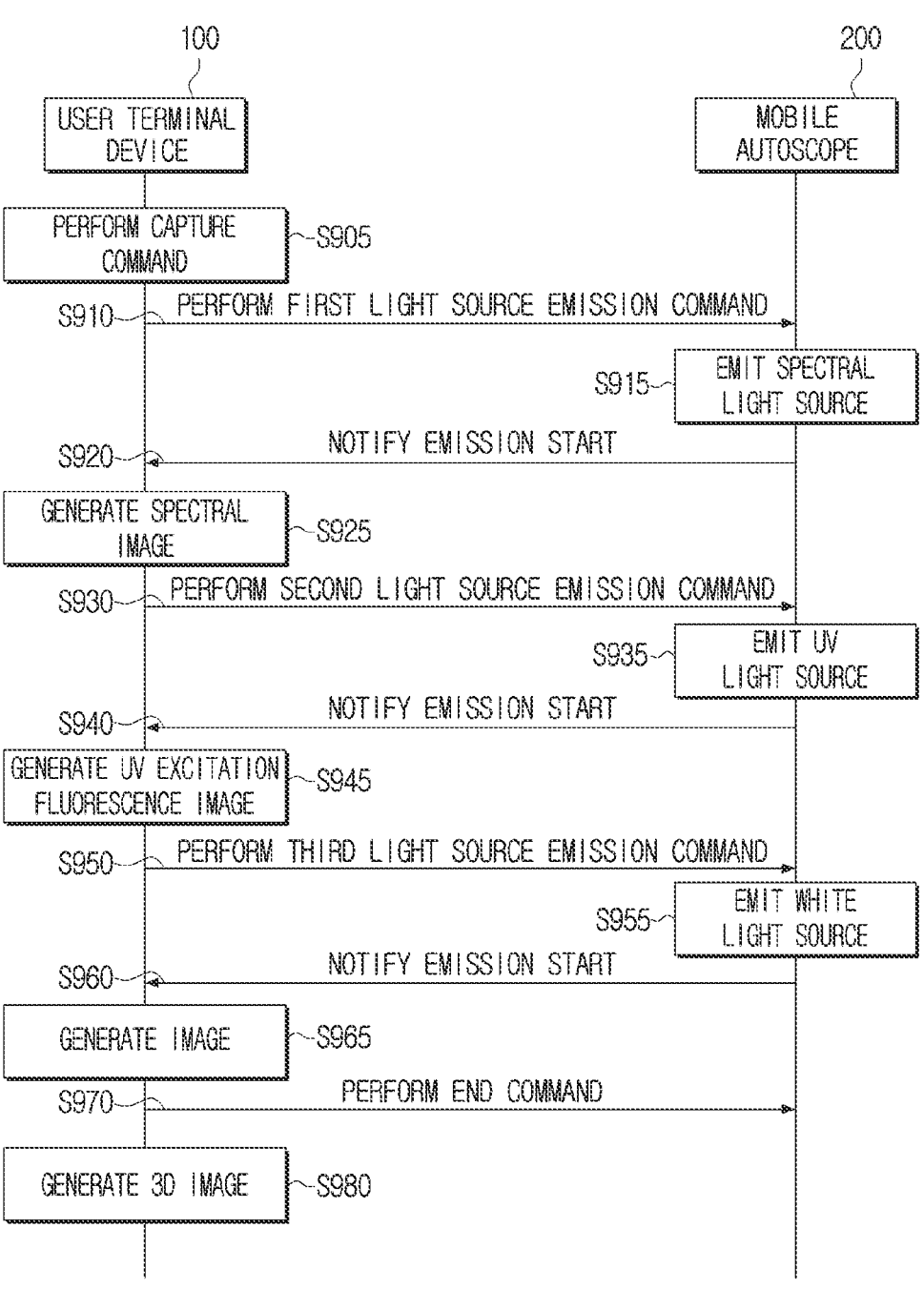

FIG. 9 is a sequence diagram for explaining an operation performed between the user terminal device and the mobile autoscope according to an embodiment of the disclosure.

Referring to FIG. 9, the capture command may be received from the user (S905). The capture command may be input through the selection of the UI displayed on the user terminal device 100, or through the button positioned on the mobile autoscope 200.

In case of receiving the capture command, the user terminal device 100 may transmit a first light source emission command to the mobile autoscope 200 (S910). Here, the first light source emission command may be an emission command for one of the UV light source, the spectral light source, and the white light source. Hereinafter, for ease of explanation, the emission command is assumed to be a spectral light source emission command.

The mobile autoscope 200, which receives the emission command, may control the lighting module for the spectral light source to emit light (S915). In case that the light emission starts, the mobile autoscope 200 may notify the user terminal device 100 that the mobile autoscope 200 performed an operation by the command, and in response, the user terminal device 100 may generate the spectral image. Meanwhile, for ease of explanation, the description hereinabove describes that the spectral image is generated in one process. However, as described above, spectral light may be generated in the process in which light in the plurality of bands different from each other are emitted to generate the images of light. Therefore, the above-described process may be performed to correspond to the number of spectral light in the system. For example, the above-described operations may be repeated a total of nine times in case that the spectral light source includes nine narrowband LEDs.

In case that the generation of the spectral image is completed, the generation process of the UV excitation fluorescence image may be performed in the same way (S930, S935, S940, and S945).

In case that the generation of the UV excitation fluorescence image is completed, the generation process of the 3D shape image may be performed in the same way (S950, S955, S960, and S965).

In case that the generation of the image using each light source is completed, the user terminal device 100 may notify the mobile autoscope 200 that the operation is completed, and reconstruct the 3D image by using the generated image (S980).

Meanwhile, the description describes that each image generation process is performed through a plurality of communication processes such as the emission command/ the emission start notification/the image generation, with reference to FIG. 9. However, the communication may be implemented to be performed only at the beginning, and the light emission and capturing operations may then be performed based on an algorithm known to both the devices. For example, the mobile autoscope 200 may perform the light emission/idle process in the predetermined order in a 0.1 second unit, and the user terminal device may also capture the image in a 0.2 second unit to correspond to the method above.

Therefore, according to a method of capturing the image in this embodiment, the image may be captured using the UV light source and the spectral light source, thus acquiring the UV image or the spectral image from which not only its morphological feature but also physiological/biological information may be checked. In addition, according to this method, the analysis may be performed using the UV image or the spectral image, thus making a more accurate and high-quality diagnosis possible.

The operation shown in FIG. 8 or 9 may be performed by the user terminal device having the configuration of FIG. 2 or the mobile autoscope having the configuration of FIG. 3, and may also be performed by a device having another configuration.

In addition, the methods for providing an image described above may be implemented by a program including an executable algorithm that may be executed in a computer, and the program may be stored and provided in a non-transitory computer readable medium.

The non-transitory computer readable medium is not a medium that temporarily stores data, such as a register, a cache, or a memory, and indicates a medium that semi-permanently stores data and is readable by a machine. In detail, the programs executing the various methods described above may be stored and provided in the non-transitory computer readable medium such as a compact disk (CD), a digital versatile disk (DVD), a hard disk, a Blu-ray disk, a universal serial bus (USB), a memory card, the read only memory (ROM) or the like.

Although the embodiments are shown and described in the disclosure as above, the disclosure is not limited to the specific embodiments described above, and may be variously modified by those skilled in the art to which the disclosure pertains without departing from the gist of the disclosure as disclosed in the accompanying claims. These modifications should also be understood to fall within the scope and spirit of the disclosure.

What is claimed is:

1. A mobile autoscope system comprising:
a user terminal device including a camera configured to capture an image of a capture target; and
a mobile autoscope detachably mounted on the user terminal device, and configured to emit each of spectral light, ultraviolet (UV) light, and white light to the capture target,
wherein the user terminal device is configured to capture the capture target during the emission of spectral light, UV light, and white light to generate a spectral image, a UV excitation fluorescence image, and a three-dimensional (3D) shape image, and
wherein the mobile autoscope further includes:
a housing having a handle area which is able to be gripped by a user,
a gripping member configured to selectively adjusting a distance between the mobile autoscope and the user terminal device by adjusting a distance between plurality of protruding members, and a motor configured to control the distance between the plurality of protruding members.

2. The system as claimed in claim 1, wherein the mobile autoscope includes
a probe configured to be in contact with the capture target;
a plurality of lenses disposed between a tip of the probe and the user terminal device, and configured to concentrate light outside the probe on the camera;
a lighting module including a spectral light source, a UV light source, and a white light source; and
an optical fiber configured to transmit light emitted from the spectral light source or the UV light source to the tip of the probe.

3. The system as claimed in claim 2, wherein the mobile autoscope further includes
a button receiving a capture command for a target object; and
a communication device configured to transmit the received capture command to the user terminal device.

4. The system as claimed in claim 2, wherein the mobile autoscope further includes a communication device configured to receive a capture command from the user terminal device, and
the mobile autoscope is configured to control the lighting module to sequentially emit spectral light, UV light, and white light in case that the capture command is received from the user terminal device.

5. The system as claimed in claim 2, wherein the UV light source includes a UV light emitting diode (LED) emitting light in a UV band, and
the mobile autoscope further includes
a first optical filter configured to bandpass filter light emitted from the UV LED, and provide filtered light to the optical fiber, and
a second optical filter configured to filter fluorescence light generated by the UV LED and transmit filtered fluorescence light to the camera.

6. The system as claimed in claim 2, wherein the spectral light source includes a plurality of narrowband LEDs having different center wavelengths.

7. The system as claimed in claim 1, wherein the user terminal device is configured to display the plurality of images of different light sources.

8. The system as claimed in claim 1, wherein the user terminal device is configured to transmit the generated plurality of images to an external server in case that the plurality of images of different light sources are generated, and
display evaluation information in case that the evaluation information on the plurality of images is received from the external server.

9. A mobile autoscope system comprising:
a user terminal device including a camera configured to capture an image of a capture target; and
a mobile autoscope detachably mounted on the user terminal device, and configured to emit each of spectral light, ultraviolet (UV) light, and white light to the capture target,
wherein the user terminal device is configured to capture the capture target during the emission of spectral light, UV light, and white light to generate a spectral image, a UV excitation fluorescence image, and a three-dimensional (3D) shape image,
wherein the mobile autoscope includes
a probe configured to be in contact with the capture target;

a plurality of lenses disposed between a tip of the probe and the user terminal device, and configured to concentrate light outside the probe on the camera;

a lighting module including a spectral light source, a UV light source, and a white light source; and an optical fiber configured to transmit light emitted from the spectral light source or the UV light source to the tip of the probe, and wherein the white light source includes a plurality of white LEDs disposed at the tip of the probe.

* * * * *